(12) United States Patent
Lee et al.

(10) Patent No.: US 6,869,447 B2
(45) Date of Patent: Mar. 22, 2005

(54) PROSTHETIC KNEE IMPLANT WITH MODULAR AUGMENT

(75) Inventors: Chelynne Nicole Lee, Warsaw, IN (US); Donald Steven Block, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/327,526

(22) Filed: Dec. 20, 2002

(65) Prior Publication Data

US 2004/0122521 A1 Jun. 24, 2004

(51) Int. Cl.⁷ .................................................. A61F 2/38
(52) U.S. Cl. ............................. 623/20.15; 623/20.28; 623/20.31
(58) Field of Search ........................... 623/20.14, 20.15, 623/20.17, 20.28, 20.29, 20.31

(56) References Cited

U.S. PATENT DOCUMENTS

| | | | | |
|---|---|---|---|---|
| 4,936,847 A | * | 6/1990 | Manginelli | 623/20.16 |
| 5,152,796 A | * | 10/1992 | Slamin | 623/20.15 |
| 5,531,793 A | | 7/1996 | Kelman et al. | |
| 5,556,433 A | * | 9/1996 | Gabriel et al. | 623/20.36 |
| 5,683,472 A | * | 11/1997 | O'Neil et al. | 623/20.31 |
| 5,944,756 A | * | 8/1999 | Fischetti et al. | 623/23.15 |
| 6,126,693 A | * | 10/2000 | O'Neil et al. | 623/20.32 |
| 6,171,342 B1 | | 1/2001 | O'Neil et al. | |
| 6,423,096 B1 | * | 7/2002 | Musset et al. | 623/20.15 |
| 6,527,807 B1 | * | 3/2003 | O'Neil et al. | 623/20.15 |
| 6,613,092 B1 | * | 9/2003 | Kana et al. | 623/20.15 |
| 6,629,978 B2 | * | 10/2003 | Schulzki et al. | 606/86 |

FOREIGN PATENT DOCUMENTS

EP  0985386 A  3/2000

OTHER PUBLICATIONS

P.F.C. Sigma Knee System — Revision Surgical Technique Specialist 2 Instruments Brochure.
European Search Report.

* cited by examiner

Primary Examiner—Corrine McDermott
Assistant Examiner—Suzette J. Jackson

(57) ABSTRACT

A modular prosthetic knee implant system includes a femoral component, a femoral stem, a femoral stem collar, an augment and a bolt. The modular prosthetic knee system can be assembled in different ways. If assembled without the augment, the stem is at a valgus angle. If assembled with the augment, the stem is at a neutral angle. The stem collar has an inferior surface that is angled with respect to its superior surface, and the augment has a superior surface that is angled with respect to its inferior surface. The components also include mating anti-rotation members to fix the relative positions of the members.

18 Claims, 8 Drawing Sheets

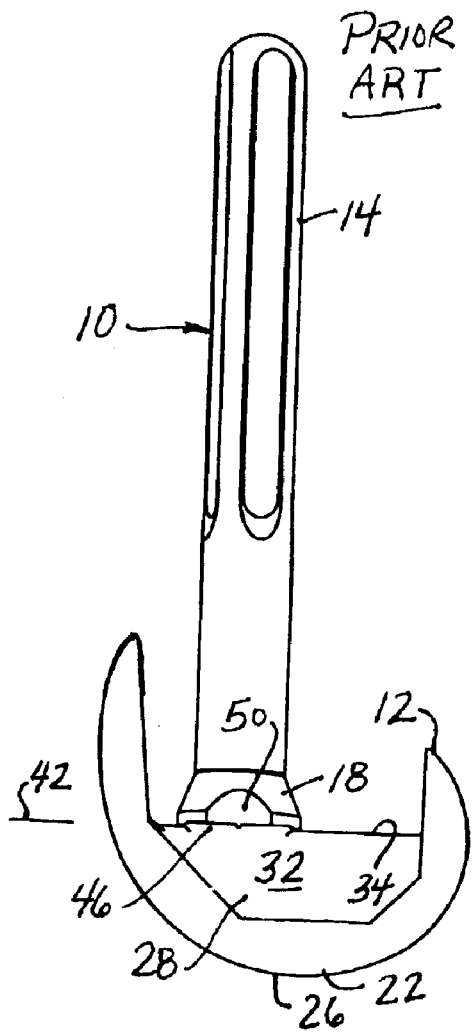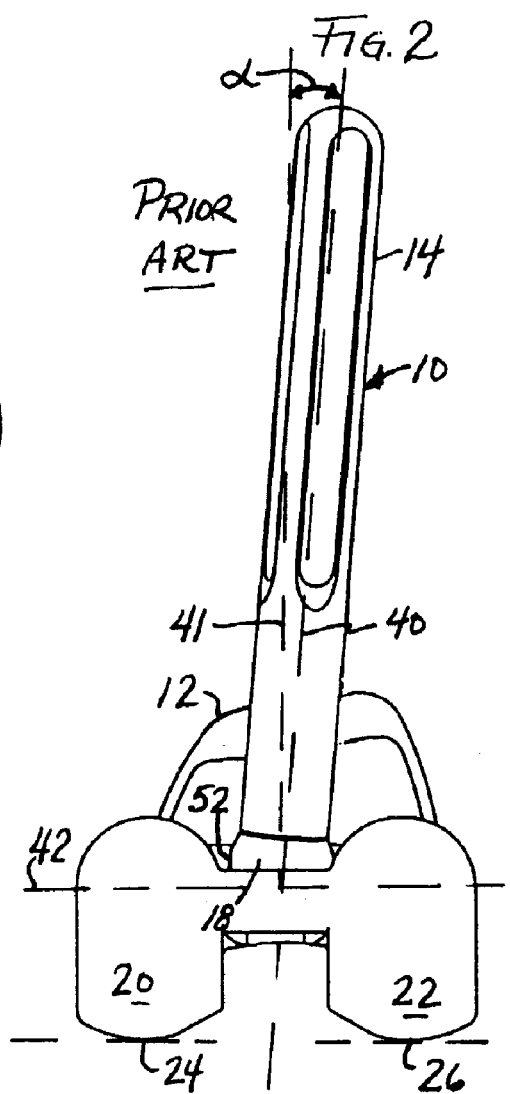

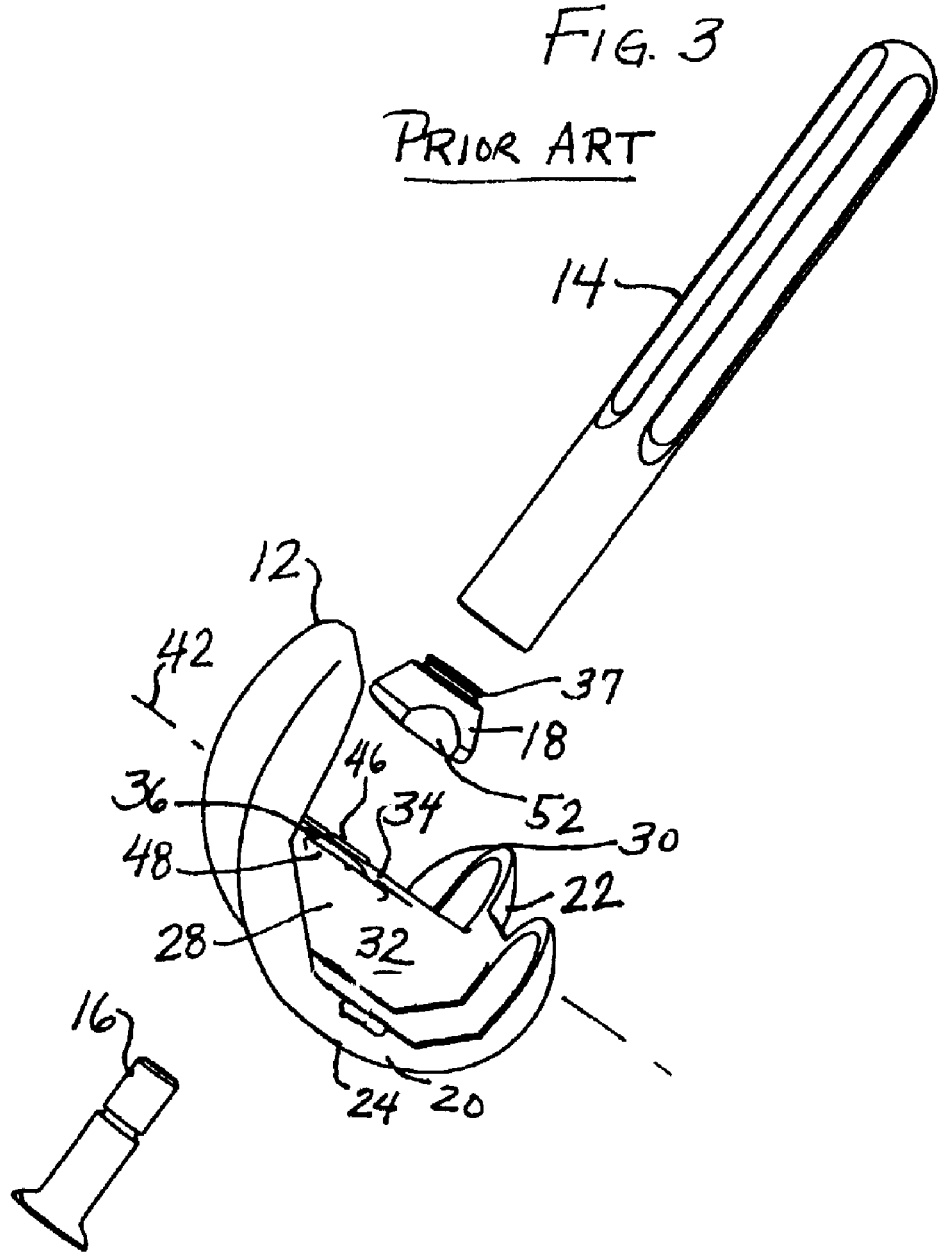

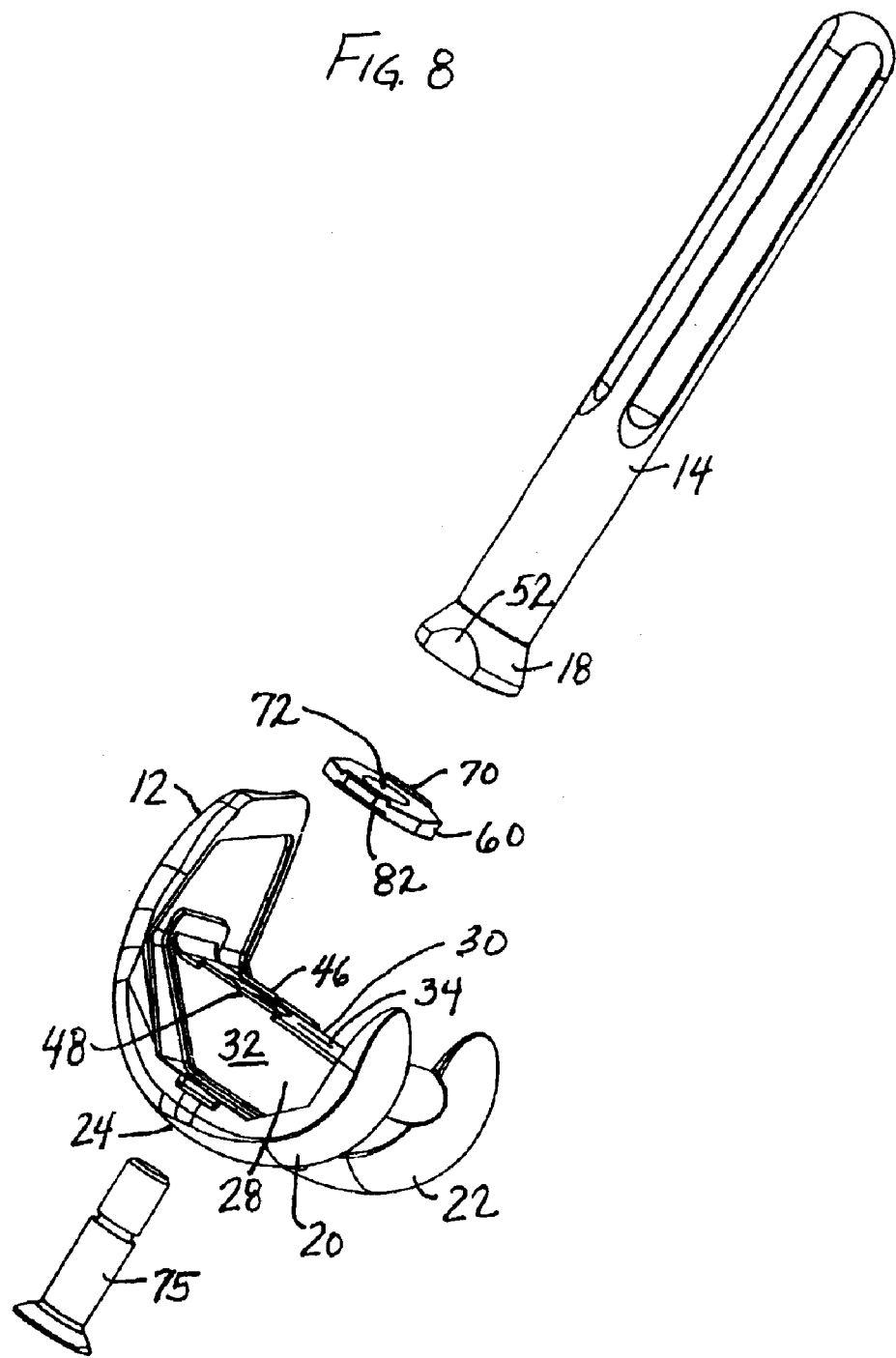

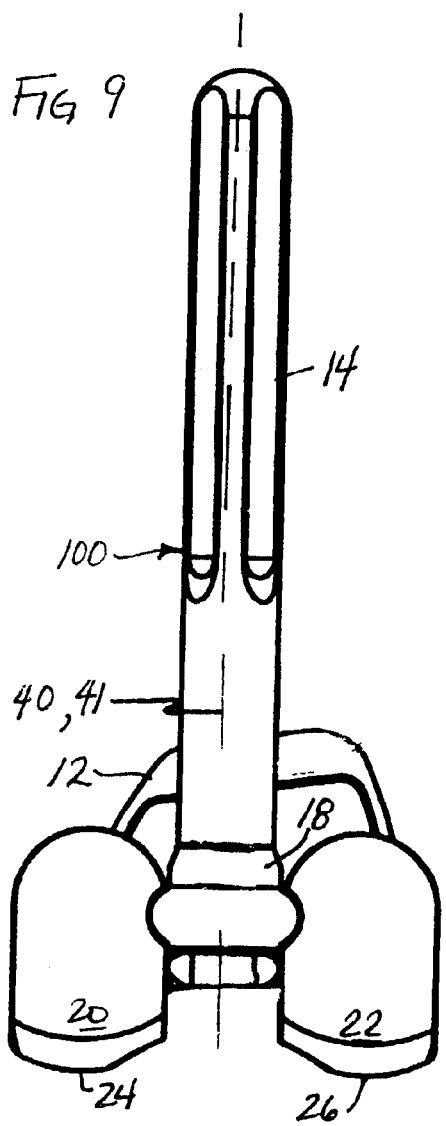
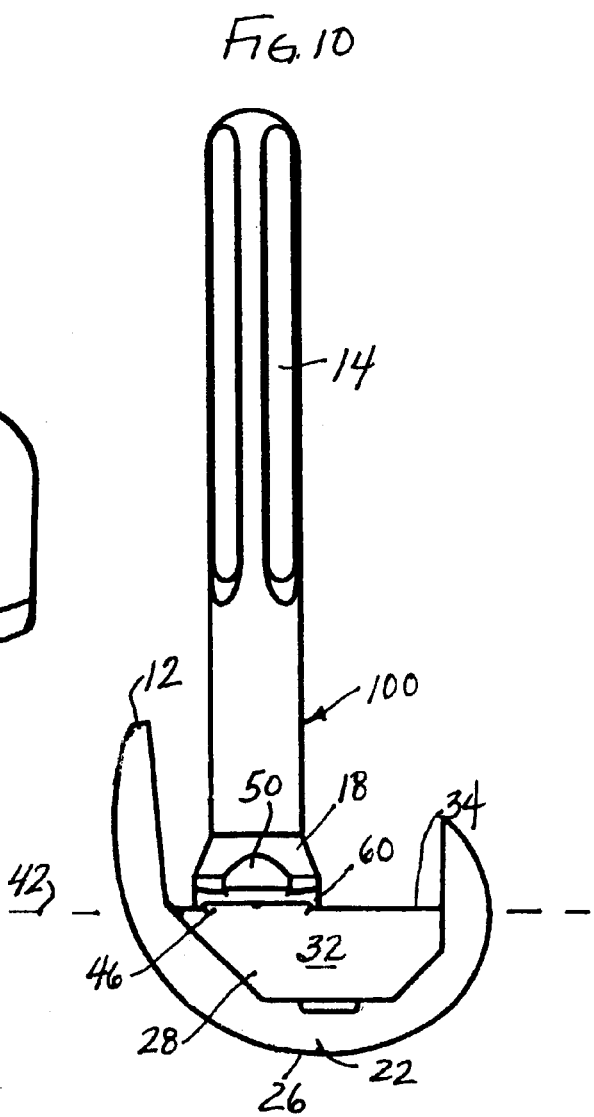

PROSTHETIC KNEE IMPLANT WITH MODULAR AUGMENT

BACKGROUND OF THE INVENTION

The present invention relates to modular components of a prosthetic joint, and more particularly to modular components of a prosthetic knee joint.

The knee joint basically consists of the bone interface of the distal end of the femur and the proximal end of the tibia. Appearing to cover or at least partially protect this interface is the patella, which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle), which are substantially, smooth and articulate with the medial plateau and the lateral plateau of the tibia, respectively. The plateaus of the tibia are substantially smooth and slightly cupped thereby providing a slight receptacle for receipt of the femoral condyles.

When the knee joint is injured whether as a result of an accident or illness, a prosthetic replacement of the damaged joint may be necessary to relieve pain and to restore normal use to the joint. Typically the entire knee joint is replaced by means of a surgical procedure, which involves removal of the ends of the corresponding damaged bones and replacement of these ends with prosthetic implants. This replacement of a native joint with a prosthetic joint is referred to as a primary total-knee arthroplasty.

Prosthetic knee implants include femoral implants that are designed to be affixed to the distal end of the resected femur. A known modular femoral implant is illustrated in FIGS. 1–3. As there shown, the modular femoral implant 10 includes a femoral component 12, an elongate stem member 14, bolt 16 (shown in FIG. 3), and a femoral stem collar 18.

The modular femoral component 12 includes two spaced condylar portions 20, 22 with articulating surfaces 24, 26 to engage an articulating surface of a tibial implant (not shown). On the proximal side of the femoral component 12, the two condylar portions 20, 22 are connected by an intercondylar box or pad 28. The intercondylar box or pad 28 has a pair of substantially vertical side walls 30, 32 that are connected by a top or superior seating or mounting platform 34. The pad mounting platform 34 is generally planar, and has an opening 36 (see FIG. 3) that extends through the pad to define an open channel. The bolt 16 extends through the channel from the distal side of the femoral component and through the opening 36 to be connected to a female threaded opening in the femoral stem 14.

The femoral stem collar 18 has a threaded male portion 37 (FIG. 3) for connection to a distal female threaded end of the stem member 14. Thus, the stem member 14, stem collar 18 and femoral component 12 can be assembled to secure the stem member 14 to the femoral component 12. With this design, a variety of styles and sizes of stem members and femoral components can be assembled to best suit the patient's anatomy and joint conditions. For example, an implant kit could include a set of different sizes of stem members with outer surfaces adapted for cemented implantation as well as with fluted outer surfaces.

As shown in FIG. 2, when assembled, the stem member 14 is typically angled in a medial direction. The angle is labeled in FIG. 2 as α. The angle α is between the axis 40 of the stem member 14 and a line 41 perpendicular to the plane 42 of the seating or mounting platform 34 of the intercondylar pad or box 28. The angle α corresponds with the valgus angle when the implant assembly is implanted; the valgus angle is defined as the angle between the center line of the femur and the vertical axis connecting the distal femur and the center of the femoral head; the center line of the femur will correspond with the axis 40 of the stem member 14, and the vertical axis connecting the distal femur and the center of the femoral head will correspond with the line 41.

In the illustrated prior art modular assembly, the angle α is set by the structure of the femoral stem collar 18. The femoral stem collar has a superior side or surface 33 lying in a plane and an inferior side or surface 35 lying in a plane that is not parallel to the plane of the superior side or surface 33. The inferior surface of the collar is angled, defining an obtuse angle (90°+α) with the axis 40 of the stem. In typical implant sets, a plurality of femoral stem collars 18 are provided, shaped so that the angle α can be set to be any one of a number of angles. In one implant set available from DePuy Orthopaedics, Inc. of Warsaw, Ind., the femoral stem collars are shaped to define angles α of either 5° or 7°, but angles α may be in a typical range of 5–9°.

Although not shown in FIGS. 1–3, the illustrated prior art stem collar 18 has a central bore to receive part of the bolt 16. The central bore has a central longitudinal axis defining an obtuse angle with at least one of the plane of the superior side 33 and inferior side 35 of the stem collar 18.

To ensure that the angle α remains in the illustrated orientation, the intercondylar box or pad 28 typically has a pair of anti-rotation tabs 46, 48 (see FIGS. 1 and 3) that mate with opposing flats 50, 52 on the femoral stem collars 18.

As commercially supplied, the stem members 14 and stem collars 18 are supplied as a unit, connected together prior to being supplied to the surgeon.

Reference is made to the implant systems disclosed in U.S. Pat. Nos. 5,683,472 and 6,126,693, which are both incorporated by reference herein in their entireties.

Although the illustrated prior art system is versatile and economic, in some instances, it may be desirable to implant the femoral components with a neutral valgus angle.

SUMMARY OF THE INVENTION

The present invention provides an enhancement to prior art implant systems by allowing for setting the femoral stem member of a modular implant assembly at a neutral valgus angle.

In one aspect, the present invention serves this purpose by providing a modular prosthetic knee implant system comprising a femoral component, a stem member, a stem collar and an augment. The femoral component includes a pair of condylar portions and an intercondylar portion having a mounting platform. The stem collar has a superior side and an inferior side. In addition, the augment has a superior side and an inferior side. The femoral component, stem member and stem collar are capable of being assembled so that the stem member is in a first fixed angular relationship with the mounting platform. The femoral component, stem member, stem collar, and augment are also capable of being assembled so that the stem member is in a second fixed angular relationship with the mounting platform.

In another aspect, the present invention provides a modular prosthetic knee implant system comprising a femoral component, a stem member, a stem collar, and an augment.

The femoral component has a pair of condylar portions and an intercondylar portion. The intercondylar portion has a mounting platform; at least part of the mounting platform lies in a plane. The stem collar has a superior side and an inferior side; at least part of the superior side and at least part of the inferior side lie in separate non-parallel planes. The stem collar also has a bore extending from the superior side to the inferior side; the bore has a central longitudinal axis that defines an obtuse angle with at least one of the plane of the superior side and the plane of the inferior side of the stem collar. The augment has a superior side and an inferior side; at least part the superior side and at least part of the inferior side of the augment lie in separate non-parallel planes. The augment also has a bore extending from the superior side to the inferior side; the bore has a central longitudinal axis that defines an obtuse angle with at least one of the plane of the superior side and the plane of the inferior side. The stem collar, augment and mounting platform of the femoral component further include mating anti-rotation members.

In another aspect, the present invention provides a modular augment for use with a prosthetic knee implant. The modular augment has a body with a superior side and an inferior side. At least a portion of the superior side of the augment lies in a superior plane. At least a portion of the inferior side of the augment lies in an inferior plane. A bore extends from the superior side to the inferior side of the augment. The bore has a central longitudinal axis that defines an obtuse angle with at least one of the superior plane and inferior plane.

In another aspect, the present invention provides a prosthetic knee implant comprising a femoral component, an augment, a stem collar, a stem and a bolt. The femoral component includes a pair of condylar portions and an intercondylar portion having a mounting platform with an opening. The augment has an inferior side on the mounting platform of the femoral component and a superior side; the augment also has a bore extending from the superior side to the inferior side. The stem collar has an inferior side on the superior side of the augment and a superior side; the stem collar also has a bore extending from the superior side to the inferior side and aligned with the bore of the augment. The stem member extends outward from the superior side of the stem collar. The bolt extends through the opening in the mounting platform of the intercondylar portion of the femoral component, through the bore of the augment and the bore of the stem collar to the stem member.

BRIEF DESCRIPTION OF THE DRAWINGS

A prior art modular femoral implant and a modular femoral implant incorporating the principles of the present invention are illustrated in the accompanying drawings, where like reference numbers are used for like parts and wherein:

FIG. 1 is an elevation of a prior art modular femoral implant, shown assembled and from the lateral side;

FIG. 2 is an elevation of the prior art modular femoral implant of FIG. 1, shown assembled and from the posterior side;

FIG. 3 is an exploded view of the prior art modular femoral implant of FIGS. 1–2;

FIG. 8 is an exploded view of a femoral implant assembly combining the femoral stem augment of FIGS. 4–7 with the prior art femoral implant components of FIGS. 1–3;

FIG. 9 is an elevation of the femoral implant assembly combining the femoral stem augment of FIGS. 4–7 with the prior art femoral implant components of FIGS. 1–3, shown from the posterior side;

FIG. 10 shows the femoral implant assembly of FIG. 9 from the lateral side;

DETAILED DESCRIPTION OF THE INVENTION

A femoral stem augment incorporating the principles of the present invention is illustrated in FIGS. 4–12 at 60. The femoral stem augment 60 of the present invention may be used with commercially available prosthetic knee components, as shown in FIGS. 8–12, where the same reference numbers for prior art components and features of components are used as were used above in describing the prior art illustrated in FIGS. 1–3.

Figure 4:
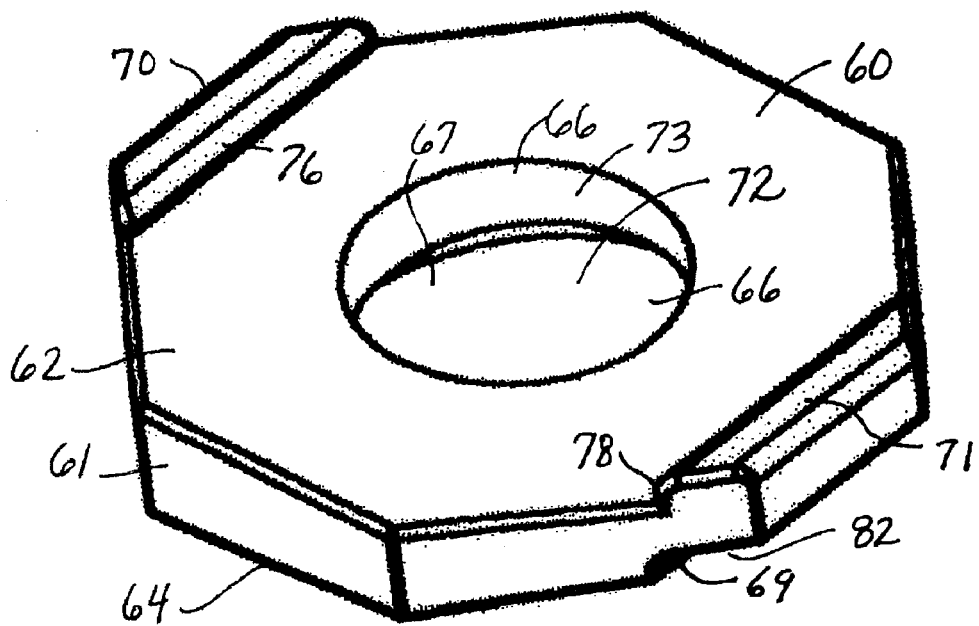
FIG. 4 is a perspective view of a femoral stem augment incorporating the principles of the present invention.
Figure 5:
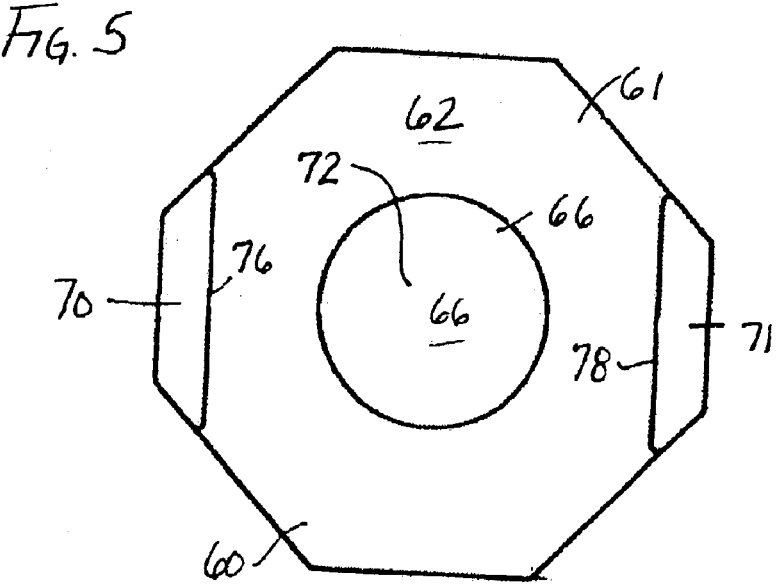
FIG. 5 is a top plan view of the femoral stem augment of FIG. 4.
Figure 6:
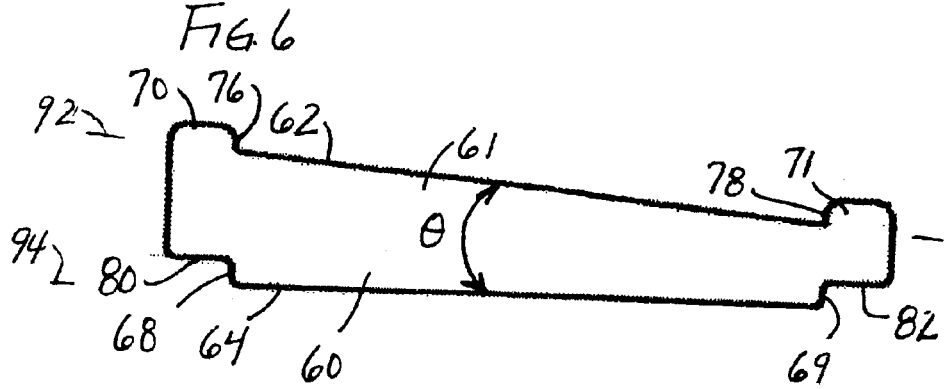
FIG. 6 is a side elevation of the femoral stem augment of FIGS. 4–5.
Figure 7:
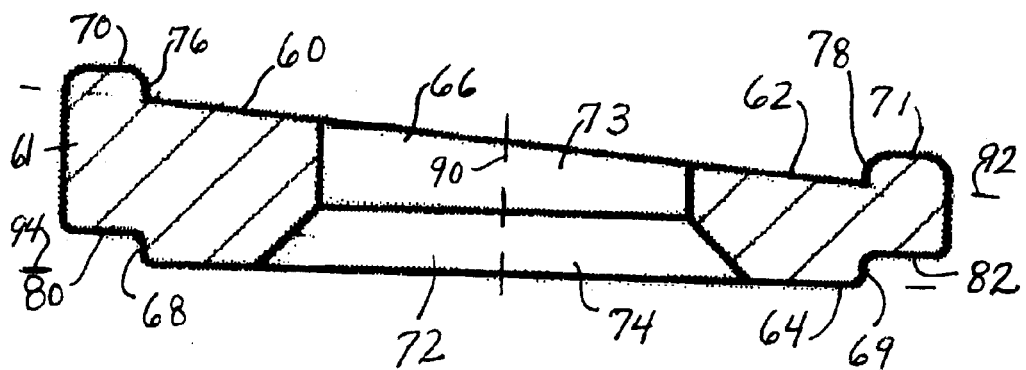
FIG. 7 is a cross-section of the femoral stem augment of FIGS. 4–6, taken along line 7—7 of FIG. 5.
Figure 11:
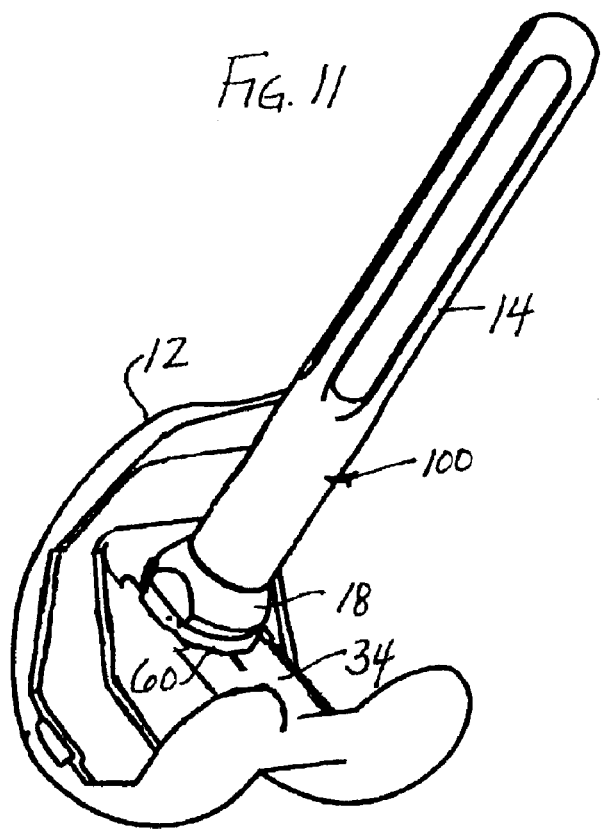
FIG. 11 is a perspective view of the femoral implant assembly of FIGS. 8–10.
Figure 12:
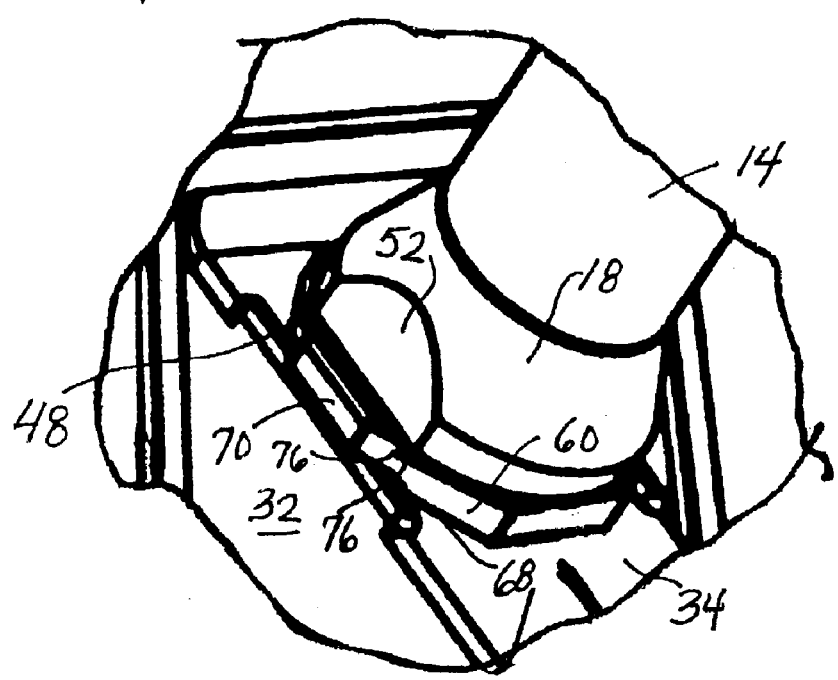
FIG. 12 is an enlarged perspective view of the femoral implant assembly of FIG. 11, showing the connection of the components.
Figure 13:
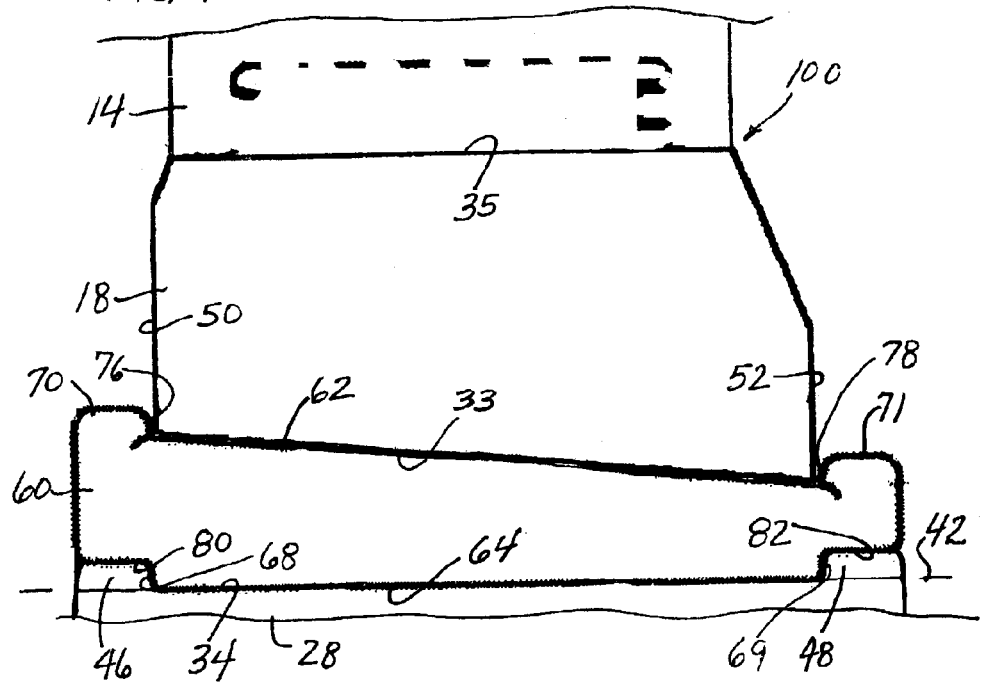
FIG. 13 is an enlarged side elevation of a portion of an assembly of a femoral component, femoral stem, femoral stem collar and augment.

As shown in FIGS. 4–7, the femoral stem augment 60 comprises a body 61 having a superior side 62 and an inferior side 64. As shown in FIGS. 6–7, the superior side 62 of the augment 60 lies in a superior plane and the inferior side 64 lies in a non-parallel inferior plane. The femoral stem augment has a central opening 66 in the superior side 62, an enlarged-diameter opening 67 in the inferior side 64, a pair of inferior anti-rotation flats 68, 69 and a pair of superior anti-rotation tabs 70, 71.

As shown in FIGS. 4–5, the illustrated femoral stem augment 60 has an overall octagonal shape, in plan view, as illustrated in FIGS. 4–5. However, it should be understood that this shape is provided for purposes of illustration only. The present invention is not limited to any particular shape of femoral stem augment 60 unless expressly called for in the claims.

In elevation, the illustrated femoral stem augment 60 has a wedge shape, as shown in FIGS. 6–7. As there shown, the superior surface 62 of the augment 60 defines an angle θ with the inferior surface 64. The angle θ corresponds with one of the valgus angles provided by the femoral stem collars 18. For example, if an implant kit includes femoral stems and collars 18 defining angles of 5° and 7°, then the stem augment 60 should be provided to define a counter angle of either 5° and 7°. Although a kit could include stem augments 60 of both angles, only one set of augments with one angle should be necessary since the kit would generally include a complete set of stem members in both the 5° and 7° sizes.

In the illustrated embodiment, a bore or channel 72 extends between the apertures or openings 66, 67 of the femoral stem augment. The bore or channel 72 has a superior cylindrical portion 73 and an inferior frusto-conical portion 74. The illustrated frusto-conical portion 74 defines a countersink at the opening 67 in the inferior side 64 of the augment 60. The illustrated channel 72 has smooth inner walls. A bolt 75 can extend through this channel 72 to connect to the prior art femoral stem collar 18. The bolt 75 is similar to the bolt 16 of the prior art, but is slightly longer to accommodate the extra distance provided by the femoral stem augment 60.

Figure 14:
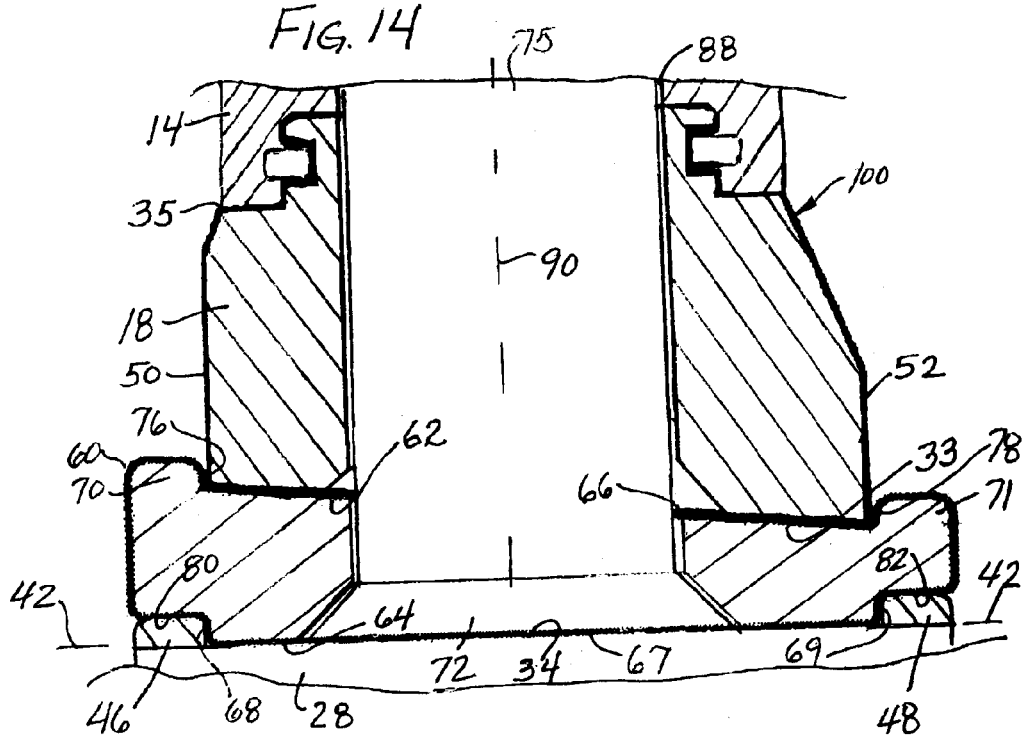
FIG. 14 is a cross-section of the assembly of FIG. 13.

As shown in FIG. 7, the bore or channel 72 has a central longitudinal axis 90 that defines an obtuse angle with at least one of the superior plane 92 and inferior plane 94 of the augment. As shown in FIG. 14, when the augment 60 is assembled with the stem collar 18, the bores of the two components share a single co-linear central longitudinal axis 90 that also defines an obtuse angle with respect to the plane of the inferior surface 33 of the stem collar 18.

The anti-rotation tabs 70, 71 of the illustrated femoral stem augment 60 define parallel flat surfaces 76, 78. These two parallel flat surfaces 76, 78 are positioned opposite to one another in the illustrated embodiment, and are spaced by a distance slightly greater than the distance between the flats 50, 52 of the femoral stem collars 18, and substantially equal to the distance between facing opposing surfaces of the anti-rotation tabs 46, 48 of the intercondylar pad or box 28. Thus, when the components are assembled as shown in FIGS. 9–12, the flats 50, 52 of the femoral stem collars 18 are received between the parallel flat surfaces 76, 78; these flats 50, 52, 76, 78 prevent relative rotation between the femoral stem collar 18 and the femoral stem augment 60.

The inferior anti-rotation flats 68, 69 of the illustrated femoral stem augment 60 are defined by undercuts 80, 82 in the femoral stem augment 60 beneath the tabs 70, 71. The inferior anti-rotation flats 68, 69 are generally parallel to each other, and are positioned opposite to one another in the illustrated embodiment. The undercuts 80, 82 are aligned with the tabs 70, 71, each undercut lying between one tab and the inferior plane 94 of the body 61 of the augment.

The distance between the inferior anti-rotation flats 68, 69 is substantially equal to the distance between the flats 50, 52 of the femoral stem collars and slightly smaller than the distance between facing opposing surfaces of the anti-rotation tabs 46, 48 of the intercondylar pad or box 28. Thus, when the components are assembled as shown in FIGS. 9–12, the anti-rotation flats 68, 69 are received between the facing surfaces of the anti-rotation tabs 46, 48 of the intercondylar box or pad 28, and the tabs 70, 71 of the femoral stem augment 60 overlie the tabs 46, 48 of the intercondylar box or pad 28.

The other components of the femoral implant may be commercially available ones. The femoral stem members 14, femoral collars 18 and femoral components 12, as well as the tibial and patellar implants, can be those commercially available from DePuy Orthopaedics, Inc. of Warsaw, Ind., sold as the P.F.C.® SIGMA and P.F.C.® SIGMA RP Knee System. Typically, a modified system would include all of the standard elements of the currently available P.F.C.® SIGMA and P.F.C.® SIGMA RP Knee System, along with standard augments, and with standard variations in size and surface finishes. The modified system would also include one or more stem augments 60 defining an angle θ of corresponding with one of the angles α. However, it should be understood that the present invention is not limited to any particular knee system unless expressly limited by the claims.

In use, the surgeon can prepare the proximal end of the tibia and distal end of the femur in the standard manner, and resect these bones in the standard manner to receive the prosthetic components. As part of this process, the surgeon can ream the femoral intramedullary canal to receive the proximal end of the stem member. If the patient's anatomy is standard, the surgeon can assemble the prior art components as shown in FIGS. 1–3, with the femoral implant defining a valgus angle of 5°–9°. If the patient's anatomy makes such a standard implant undersirable, the system of the present invention has the versatility to allow the surgeon to intraoperatively assemble a femoral implant with a neutral axis, that is, one in which the central longitudinal axis 40 of the stem 14 is perpendicular to the plane of the superior seating or mounting platform 34 of the intercondylar box 28.

The assembly of the femoral implant with a neutral axis is shown at 100 in FIGS. 9–14. The components 12, 14, 18, 60 and 75 may be assembled as follows. First, the stem members 14 and stem collars 18 may be assembled in a standard manner prior to the kit being supplied to the surgeon, such as with a retaining ring. This same stem/collar sub-assembly can be used whether the implant system will be used to define a valgus angle or whether a neutral axis is desired.

If a neutral axis is desired and the stem augment 60 of the system has an angle θ of 5°, then a stem/collar sub-assembly with an angle α of 5° is selected. The length and other characteristics of the stem member, such as whether it is fluted or has a particular surface finish, are selected as well.

The stem augment 60 can then be positioned on top of the mounting or seating platform 34 of the intercondylar box 28 between the stem/collar sub-assembly and the femoral component 12. The stem augment 60 is aligned so that the anti-rotation surfaces 68, 69 of its undercuts 80, 82 are received against the tabs 46, 48 of the intercondylar box 28 to stabilize and prevent relative rotation between the stem augment 60 and the femoral component 12. The inferior surface 64 of the augment rests against the superior surface of the mounting platform 34. The stem/collar sub-assembly is placed with the inferior surface 33 of the stem collar 18 against the superior surface 62 of the augment. The elements 14, 18, 60 are assembled so that the flats 76, 78 of the tabs 70, 71 of the augment are juxtaposed with the flats 50, 52 of the stem collar 18 to prevent relative rotation between the stem collar 18 and the augment 60. To secure the components 12, 14, 18, 60 together in the configuration shown, the bolt 75 is inserted from the inferior side of the intercondylar box 28 up through an opening in the mounting surface 34, through the openings 66, 67 and channel 70 of the augment, through the central bore 88 of the stem collar 18 and up into a threaded bore in the stem 14.

Although in the illustrated embodiments relative rotation is prevented through the use of flats and tabs, it should be understood that the invention is not so limited. Any form of mating anti-rotation devices could be used, and the invention should not be construed as being limited to the use of flats and tabs unless expressly called for in the claims. For example, pegs and mating holes could be used.

It should be understood that the same system could be used for patient's requiring a standard valgus angle. The surgeon can decide intraoperatively to assemble the femoral component with a stem/collar sub-assembly without using the augment 60. Thus, the system of the present invention provides versatility to the surgeon.

The augment 60 of the present invention can be made of any conventional material for orthopaedic implants, such as cobalt-chrome steel or titanium, or any other material that is in current orthopaedic use or becomes used in orthopaedic applications. The augment 60 can be made using standard manufacturing techniques, such as machining.

While only a specific embodiment of the invention has been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

We claim:

1. A modular prosthetic knee implant system comprising:
   a femoral component including a pair of condylar portions and an intercondylar portion having a mounting platform;
   a stem member;
   a stem collar having a superior side and an inferior side, at least part of the superior side and at least part of the inferior side lying in separate non-parallel planes, the stem collar further having a bore extending from the superior side to the inferior side, the bore having a central longitudinal axis defining an obtuse angle with at least one of the plane of the superior side and the plane of the inferior side;
   an augment having a superior side and an inferior side, at least part the superior side and at least part of the inferior side lying in separate non-parallel planes, the augment having a bore extending from the superior side to the inferior side, the bore having a central longitudinal axis defining an obtuse angle with at least one of the plane of the superior side and the plane of the inferior side; and
   a bolt;
   wherein the stem collar is shaped so that the femoral component, stem member, bolt and stem collar are capable of being assembled without the augment so that the stem member is in a first fixed angular relationship with the mounting platform;
   wherein the stem collar and augment are shaped so that the femoral component, stem member, stem collar, bolt and augment are capable of being assembled so that the stem member is in a second fixed angular relationship with the mounting platform; and
   wherein in the first fixed angular relationship at least part of the superior side of the stem collar lies in a plane defining an acute angle with at least part of the mounting platform and in the second fixed angular relationship at least part of the superior side of the stem collar lies in a plane that is parallel to at least part of the mounting platform.

2. The modular prosthetic knee implant system of claim 1 wherein the stem collar and femoral augment are capable of being assembled with the inferior side of the stem collar against the superior side of the augment.

3. The modular prosthetic knee implant system of claim 2 wherein the stem collar is capable of being assembled with the femoral component with the inferior side of the stem collar against the mounting platform.

4. The modular prosthetic implant system of claim 3 wherein the augment is capable of being assembled with the femoral component with the inferior side of the augment against the mounting platform.

5. The modular prosthetic knee implant system of claim 1 wherein the femoral component, stem member and augment include mating anti-rotation members to fix the position of the stem member with respect to the mounting platform when the femoral component, stem member and stem collar are assembled without the augment and to fix the position of the stem member when the femoral component, stem member, stem collar and augment are assembled.

6. A modular prosthetic knee implant system comprising:
   a femoral component including a pair of condylar portions and an intercondylar portion having a mounting platform;
   a stem member;
   a stem collar having a superior side and an inferior side; and
   an augment having a superior side and an inferior side;
   wherein the femoral component, stem member and stem collar are capable of being assembled so that the stem member is in a first fixed angular relationship with the mounting platform;
   wherein the femoral component, stem member, stem collar, and augment are capable of being assembled so that the stem member is in a second fixed angular relationship with the mounting platform;
   wherein the augment has an opening in the superior side, an opening in the inferior side and a channel extending between the openings and the augment channel has a countersink at the opening in the inferior side.

7. The modular prosthetic implant system of claim 6 wherein the augment channel has a cylindrical portion between the countersink and the opening in the superior side.

8. A modular prosthetic knee implant system comprising:
   a femoral component including a pair of condylar portions and an intercondylar portion having a mounting platform;
   a stem member;
   a stem collar having a superior side and an inferior side, at least part of the superior side and at least part of the inferior side lying in separate non-parallel planes, the stem collar further having a bore extending from the superior side to the inferior side, the bore having a central longitudinal axis defining an obtuse angle with at least one of the plane of the superior side and the plane of the inferior side; and
   an augment having a superior side and an inferior side, at least part of the superior side and at least part of the inferior side lying in separate non-parallel planes, the augment having a bore extending from the superior side to the inferior side, the bore having a central longitudinal axis defining an obtuse angle with at least one of the plane of the superior side and the plane of the inferior side;
   wherein the superior side of the augment lies in one plane and the inferior side of the augment lies in a non-parallel plane;
   wherein the femoral component, stem member and stem collar are capable of being assembled without the augment so that the stem member is in a first fixed angular relationship with the mounting platform;
   wherein the femoral component, stem member, stem collar, and augment are capable of being assembled so that the stem member is in a second fixed angular relationship with the mounting platform; and
   wherein in the first fixed angular relationship the stem member is oriented in a valgus direction and in the second fixed angular relationship the stem member is oriented in a neutral direction.

9. A modular prosthetic knee implant system comprising:
   a femoral component having a pair of condylar portions and an intercondylar portion having a mounting platform, at least part of the mounting platform lying in a plane;

a stem member;

a stem collar having a superior side and an inferior side, at least part of the superior side and at least part of the inferior side lying in separate non-parallel planes, the stem collar further having a bore extending from the superior side to the inferior side, the bore having a central longitudinal axis defining an obtuse angle with at least one of the plane of the superior side and the plane of the inferior side; and an augment having a superior side and an inferior side, at least part the superior side and at least part of the inferior side lying in separate non-parallel planes, the augment having a bore extending from the superior side to the inferior side, the bore having a central longitudinal axis defining an obtuse angle with at least one of the plane of the superior side and the plane of the inferior side;

the stem collar, augment and mounting platform of the femoral component further including mating anti-rotation members.

10. The modular prosthetic knee implant system of claim 9 wherein the mating anti-rotation members comprise:

upstanding tabs on the mounting platform of the femoral component;

opposing anti-rotation surfaces on the stem collar; and opposing anti-rotation surfaces and upstanding tabs on the augment.

11. The modular prosthetic knee implant system of claim 10 wherein the distance between the upstanding tabs on the mounting platform of the femoral component is substantially equal to the distance between the upstanding tabs on the augment.

12. The modular prosthetic knee implant system of claim 10 wherein the distance between the opposing anti-rotation surfaces on the stem collar is substantially the same as the distance between the opposing anti-rotation surfaces on the augment.

13. A modular augment for use with a prosthetic knee implant comprising:

a body including a superior side and an inferior side, at least a portion of the superior side lying in a superior plane;

at least a portion of the inferior side lying in an inferior plane;

a bore extending from the superior side to the inferior side;

the bore having a central longitudinal axis defining an obtuse angle with at least one of the superior plane and inferior plane;

the body further including opposing tabs extending beyond the superior plane of the superior side and an undercut aligned with each tab, each undercut lying between the tab and the inferior plane of the inferior side of the body.

14. A prosthetic knee implant comprising:

a femoral component including a pair of condylar portions and an intercondylar portion having a mounting platform with an opening;

an augment having an inferior side on the mounting platform of the femoral component and a superior side, at least part of the superior side and at least part of the inferior side lying in separate non-parallel planes, the augment having a bore extending from the superior side to the inferior side, wherein the bore has a central longitudinal axis that defines an obtuse angle with the plane of the superior side of the augment;

a stem collar having an inferior side on the superior side of the augment and a superior side, at least part of the superior side and at least part of the inferior side lying in separate non-parallel planes, the stem collar having a bore extending from the superior side to the inferior side and having a central longitudinal axis aligned with the central longitudinal axis of the bore of the augment, wherein the central longitudinal axis of the bore defines an obtuse angle with the plane of the inferior side of the stem collar;

a stem member extending outward from the superior side of the stem collar, the stem member having an axis; and a bolt extending through the opening in the mounting platform of the intercondylar portion of the femoral component, the bolt further extending through the bore of the augment and the bore of the stem collar to the stem member;

wherein at least part of the superior side of the augment lies in a plane that is not parallel to at least part of the mounting platform of the femoral component; and wherein at least part of the axis of the stem member is perpendicular to at least part of the mounting platform of the femoral component.

15. The prosthetic knee implant of claim 14 wherein the femoral component, augment and stem collar having mating anti-rotation members.

16. A prosthetic knee implant comprising:

a femoral component including a pair of condylar portions and an intercondylar portion having a mounting platform with an opening;

an augment having an inferior side on the mounting platform of the femoral component and a superior side, the augment having a bore extending from the superior side to the inferior side;

a stem collar having an inferior side on the superior side of the augment and a superior side, the stem collar having a bore extending from the superior side to the inferior side and aligned with the bore of the augment;

a stem member extending outward from the superior side of the stem collar; and a bolt extending through the opening in the mounting platform of the intercondylar portion of the femoral component, the bolt further extending through the bore of the augment and the bore of the stem collar to the stem member;

wherein the femoral component, augment and stem collar having mating anti-rotation members; and wherein the mating anti-rotation members comprise:

a pair of opposing tabs on the intercondylar portion;

a pair of undercuts on the augment defining anti-rotation surfaces aligned and juxtaposed with the opposing tabs on the intercondylar portion;

a pair of tabs on the augment; and a pair of anti-rotation surfaces on the stem collar aligned and juxtaposed with the tabs on the augment.

17. The prosthetic knee implant of claim 16 wherein the distance between the anti-rotation surfaces on the undercuts of the augment is substantially equal to the distance between the anti-rotation surfaces on the stem collar.

18. The prosthetic knee implant of claim 16 wherein the distance between the opposing tabs on the intercondylar portion is substantially the same as the distance between the tabs on the augment.

* * * * *